(12) United States Patent
Keating et al.

(10) Patent No.: US 12,420,280 B1
(45) Date of Patent: Sep. 23, 2025

(54) METHOD AND APPARATUS FOR CONDUCTING MULTIPLE REACTIONS

(71) Applicant: WAFFLEDX LIMITED, London (GB)

(72) Inventors: Timothy Keating, Melbourn (GB); Andrew Malloy, Melbourn (GB); Giles Sanders, Melbourn (GB); Gary Jepps, Melbourn (GB); Christofer Toumazou, London (GB)

(73) Assignee: WAFFLEDX LIMITED, London (GB)

( * ) Notice: Subject to any disclaimer, the term of this patent is extended or adjusted under 35 U.S.C. 154(b) by 0 days.

(21) Appl. No.: 19/010,420

(22) Filed: Jan. 6, 2025

(51) Int. Cl.
| | | |
|---|---|---|
| *B01L 3/00* | (2006.01) | |
| *B01L 7/00* | (2006.01) | |
| *C12Q 1/686* | (2018.01) | |
| *C12Q 1/6865* | (2018.01) | |

(52) U.S. Cl.
CPC ........... *B01L 3/502715* (2013.01); *B01L 7/52* (2013.01); *C12Q 1/686* (2013.01); *C12Q 1/6865* (2013.01); *B01L 2200/10* (2013.01)

(58) Field of Classification Search
None
See application file for complete search history.

(56) References Cited

U.S. PATENT DOCUMENTS

| | | | | |
|---|---|---|---|---|
| 2004/0144484 | A1* | 7/2004 | Fisher | B29C 65/483 156/292 |
| 2004/0264293 | A1* | 12/2004 | Laugharn, Jr. | B01F 33/403 366/127 |
| 2009/0220963 | A1* | 9/2009 | Yoon | C12Q 1/686 435/6.16 |

OTHER PUBLICATIONS

Bwambok, D. K., et al., "Adaptive Use of Bubble Wrap for Storing Liquid Samples and Performing Analytical Assays," Analytical Chemistry 2014 86 (15), 7478-7485. (Year: 2014).*

* cited by examiner

*Primary Examiner* — Matthew D Krcha
(74) *Attorney, Agent, or Firm* — Harness, Dickey & Pierce, P.L.C.

(57) ABSTRACT

A method of performing multiple parallel reactions and comprising introducing a liquid into a space between first and second flexible sheets, the liquid containing one or more reagents, applying localised pressure across the sheets in order to form a multiplicity of liquid filled wells between the sheets such that neighbouring wells are not in liquid communication with one another, causing reactions to occur in respective wells, the reactions occurring substantially independently of one another, and determining reaction results for the respective wells.

14 Claims, 5 Drawing Sheets

METHOD AND APPARATUS FOR CONDUCTING MULTIPLE REACTIONS

TECHNICAL FIELD

The present invention relates to a method and apparatus for conducting multiple reactions and in particular, though not exclusively, multiple parallel biological or chemical reactions.

BACKGROUND

Chemical and biological reactions often require a controlled reaction environment, i.e., a closed system that can exchange energy, such as heat, with the surroundings whilst not exchanging matter such as reagents with those surroundings. This is a minimal requirement for preventing cross-contamination and obtaining reproducible and accurate results independent of the surroundings.

An example of a biological reaction requiring such a closed system is the well-known Polymerase Chain Reaction (PCR). PCR can be exploited for nucleic acid detection, for example to identify short genetic sequences with a strand of DNA or RNA, and is a "gold-standard" for analysis of nucleic acids. Whilst performing traditional PCR requires sophisticated lab equipment, more recently rapid PCR processes and apparatus have become available allowing for single polynucleotide (SNP) detection in a matter of minutes.

Digital PCR (dPCR) is the so-called third generation of PCR for absolute quantification through partitioning of the reaction. An original sample is split into multiple sub-samples, e.g. thousands or more. Each of the subsamples undergoes a PCR (multiplex PCR) to amplify the copies of nucleic acid samples where present, with the amplified results being detected through probe-based fluorescence or similar techniques. By comparing the relative numbers of positive to negative reactions across the sub-samples, a quantitative rather than merely qualitative result can be obtained. dPCR has many applications including trace DNA detection, rare mutation detection, copy number variation and absolute quantification of gene expression.

dPCR is typically performed by pipetting or otherwise flowing a liquid sample into multiple wells or tubes and facilitating reactions within all of the wells in parallel, e.g. using thermocycling. It is of course important while carrying out the reactions to prevent any flow between (adjacent) reaction sites in order to ensure that the reactions and their results are truly independent.

SUMMARY

According to a first aspect of the present invention there is provided a method of performing multiple parallel reactions and comprising introducing a liquid into a space between first and second flexible sheets, the liquid containing one or more reagents, applying localised pressure across the sheets in order to form a multiplicity of liquid filled wells between the sheets such that neighbouring wells are not in liquid communication with one another, causing reactions to occur in respective wells, the reactions occurring substantially independently of one another, and determining reaction results for the respective wells.

The method may comprise applying heat to the flexible sheets sufficient to heat seal areas of the flexible sheets between neighbouring wells and where the localised pressure is applied. Heat may be applied to the flexible sheets to initiate and or facilitate said reactions. Heat may be applied thermo-cyclically. The same heat source may be used to heat seal areas of the flexible sheets and to initiate and or facilitate said reactions.

The method may comprise locating the liquid filled flexible sheets between upper and lower plates, clamping the plates across the flexible sheets in order to apply said localised pressure, and heating one or both of the plates in order to heat the flexible sheets. At least one of the plates may have a surface profile which defines the regions at which localised pressure is applied across the flexible sheets. The surface profile may define one or more regular grids.

The heat seal may be produced by a welding together of opposed regions of flexible sheets.

The said space may be one of a plurality of spaces formed between said flexible sheets, the spaces being separated from one another by pre-formed joins between the flexible sheets and the method being such that a multiplicity of wells are formed within each space. The joins and optionally further joins may define one or more channels extending between each space and an associated liquid inlet port, i.e. to define one or more flow paths for filling the spaces.

An inner surface of at least one of the flexible sheets may be coated a priori with a reagent or reagents to facilitate said reactions, said inner surface being opposed to an inner surface of the other of the flexible sheets. Different reagents may be coated on the inner surface within respective different spaces to permit different reactions to occur within the wells of different spaces.

The step of determining reaction results for the respective wells may comprise an optical detection process, and at least one of said flexible sheets may be a substantially optically transparent flexible sheet to permit optical detection across the substantially optically transparent flexible sheet. The plate opposed to the substantially optically transparent flexible sheet may be substantially optically transparent.

The flexible sheets may be of an inert material, optionally polypropylene.

The reactions may comprise nucleic acid amplification. For example, PCR, NASBA, reverse transcription, or LAMP. The or each reagent with which the inner surface is coated may be a primer.

The reaction results may provide a digital, quantitative result.

The step of determining reaction results for the respective wells may comprise a step of determining a number of wells within the or each space within which a common reaction result has occurred.

According to a second aspect of the present invention there is provided a system for performing multiple parallel reactions, the system comprising first and second flexible sheets configured to define a space between the sheets, a liquid supply mechanism for filling said space with a liquid containing one or more reagents, a pressure applicator for applying localised pressure across the sheets after filling of the space in order to form a multiplicity of liquid filled wells between the sheets such that neighbouring wells are not in liquid communication with one another, and a detector for detecting the results of reactions occurring within respective wells, the reactions occurring substantially independently of one another.

The system may comprise a heat source for applying heat to the flexible sheets sufficient to heat seal areas of the flexible sheets between neighbouring wells and where the localised pressure is applied.

The pressure applicator may comprise upper and lower plates configured to be clamped across the flexible sheets in order to apply said localised pressure, and a heater for heating one or both of the plates.

The system may comprise a controller configured to operate the heater to provide thermos-cyclical heating to the plate.

At least one of the upper and lower plates may have a surface profile which defines the regions at which localised pressure is applied across the flexible sheets, optionally said surface profile defining one or more regular grids.

The first and second flexible sheets may be configured to define a plurality of spaces between the sheets separated by joins, and said liquid supply mechanism being configured to fill different spaces independently of one another.

The first and second flexible sheets may be configured within a cartridge, and said liquid supply mechanism, pressure applicator and detector forming part of an analyser unit, the analyser unit being configured to removably receive the cartridge.

DETAILED DESCRIPTION

The following disclosure relates to a method of performing parallel reactions. It is suitable for applications where it is desired to have closed reaction conditions, i.e., can exchange energy such as heat, but not matter, with the surroundings. The method comprises introducing a liquid into a space formed between a pair of flexible sheets. The liquid may contain reagents for the reactions, e.g. it may comprise a buffer solution plus one or more reagents.

Figure 1A:
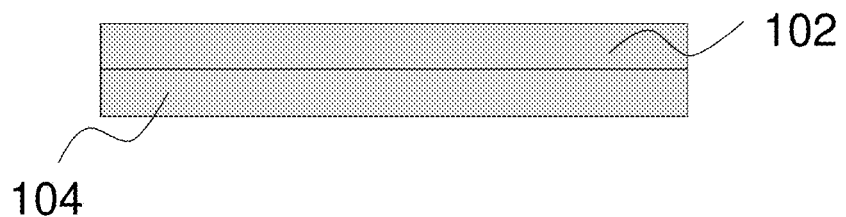
FIGS. 1a to 1c illustrate schematically the formation of multiple wells between two flexible sheets.
Figure 1B:
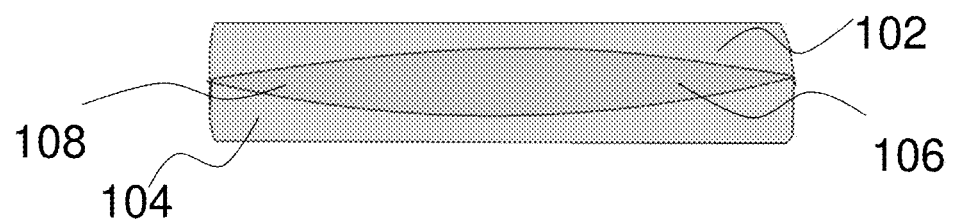
Figure 1C:
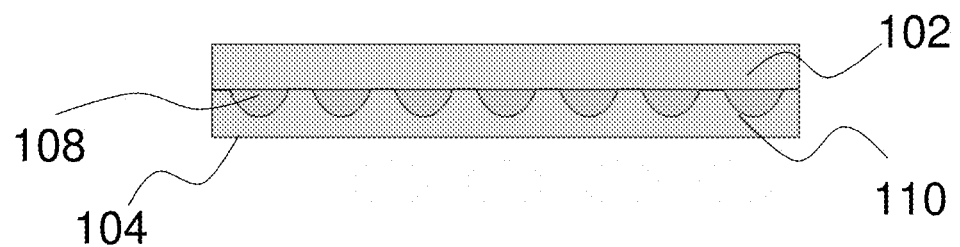

To create closed reaction conditions, the flexible sheets are sealed, after the space has been filled, using pressure to form multiple isolated wells. To form the multiplicity of liquid filled wells localized pressure is applied across the sheets such that wells sealed from one another, i.e. neighbouring wells are not in liquid communication with one another. FIG. 1 illustrates two flexible sheets 102 and 104 (FIG. 1a) forming a space 106 for introducing a liquid 108 (FIG. 1b) and a multiplicity of liquid filled wells 110 formed between the flexible sheets (FIG. 1c).

The method can therefore be used to create multiple reaction containers, i.e. wells, within which independent reactions can be performed simultaneously. The fixed size and sealed wells prevent variations in reaction conditions and cross-contamination across the reactions.

Whilst the application of pressure alone may be sufficient to seal the wells, sealing may be enhanced by applying localised heat to the flexible sheets where the localised pressure is applied. The flexible sheets may be composed of thermoplastic material or coated with a thermoplastic material at specific regions, such that localised heating creates a seal by welding or otherwise joining together the opposed and contacting regions of the flexible sheets. The weld formed may be, for example, a so called "tack weld".

The method may be used to create reaction compartments within which thermally induced reactions may be performed, i.e., heat may be used to initiate and/or facilitate said reactions. Optionally, the same heat source may be used for both heat-sealing the wells and for initiating and/or facilitating the reactions. The source and process of heating may vary according to the desired application of the method. For example, thermal-cycler based heating may be applied to maintain and regulate precise temperatures in a controlled manner using pre-programmed settings.

Figure 2A:
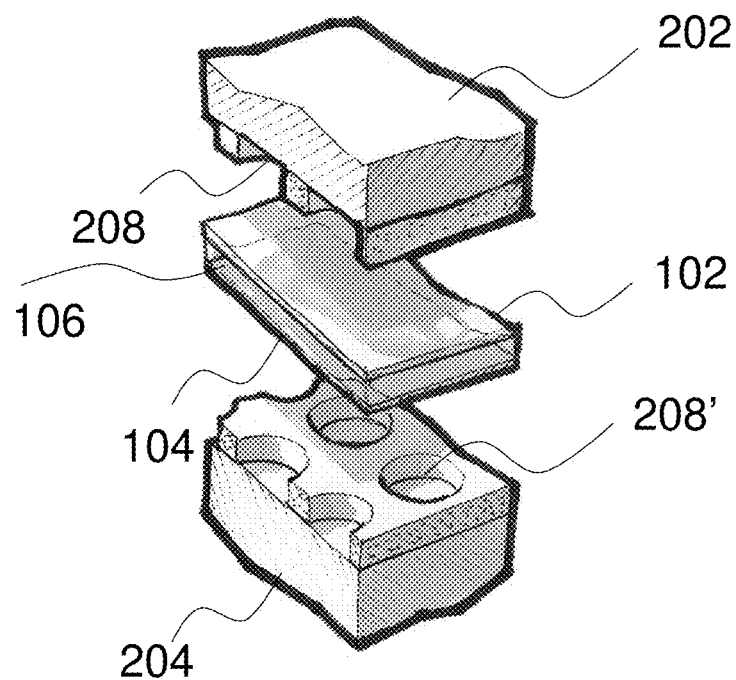
FIGS. 2a and 2b illustrate schematically a clamping mechanism suitable for forming multiple wells between two flexible sheets.
Figure 2B:
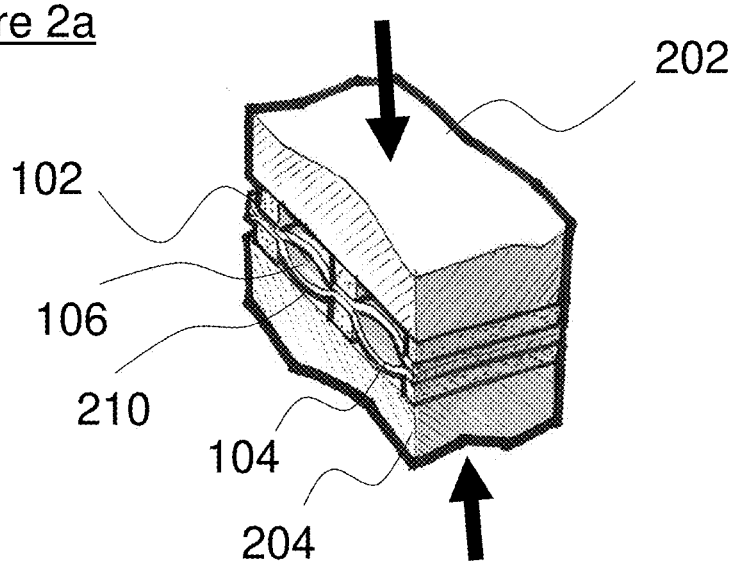

FIG. 2 illustrates the use of a pair of clamping plates, i.e. an upper clamping plate 202 and a lower clamping plate 204, to apply the required localized pressure to the liquid filled flexible sheets. The apparatus may further include a heat source for heating the one or both the plates in order to heat the flexible sheets at at least those regions where the localised pressure is applied.

One of the approaches for providing the localized pressure and/or heating may further include forming the plates such that one or both plates have a surface profile which defines the regions at which localised pressure and/or heat can be applied across the flexible sheets. Such surface profiles may be regular, i.e. defining one or more regular grids. FIG. 2 illustrates a case where cylindrical recesses are provided across the inwardly facing surfaces of the upper and lower plates according to a regular grid, with the recesses on both plates being aligned in the same horizontal plane. The prefilled sheets are squeezed between the plates to form liquid filled wells.

Figure 3A:
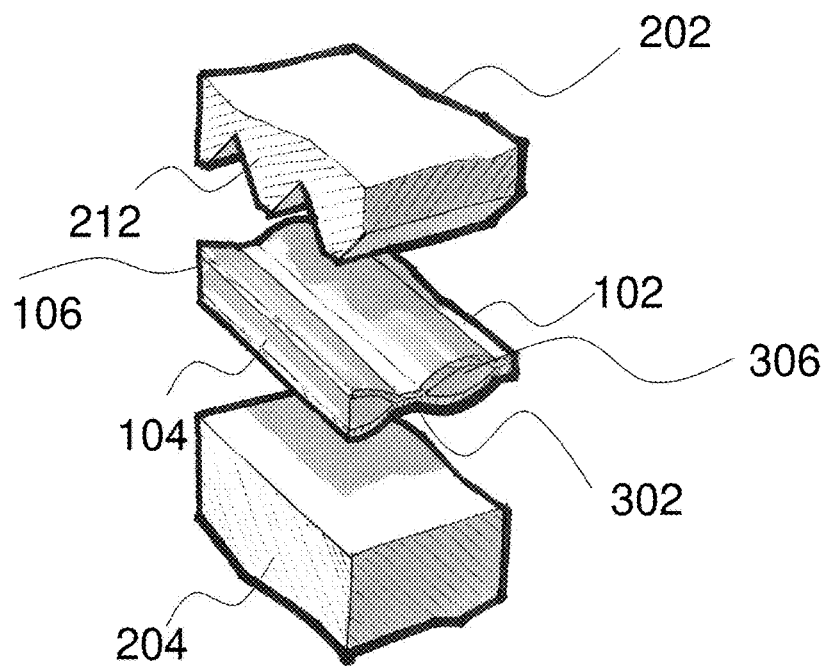
FIGS. 3a and 3b illustrate schematically an alternative clamping mechanism suitable for forming multiple wells between two flexible sheets having pre-formed joins.

A modified method and apparatus requires a preforming of the flexible sheets, prior to filling, to form compartments/sub-spaces 306. This is illustrated in FIG. 3a where multiple parallel preformed joins extend in one direction. The preformed joins ensure that each of the sub-spaces is separated from another and not in the liquid communication with the adjacent sub-space. To facilitate addition and/or exchange of liquids, each of the sub-spaces 306 may be further associated with one or more inlet/outlet ports. The method can then be used for buffer exchange for changing reaction conditions and/or for adding reagents using one or more ports. Thus, a liquid containing a different set of reagents may be introduced in each of the sealed sub-spaces enabling carrying out different reactions simultaneously. To form multiplicity of wells 210 in each of the sub-space the localised pressure may be applied to pre-formed/pre-welded flexible sheets. Thus, the method can carry out multiple independent reactions with different liquids in each of the sub-space partitioned to form a multiplicity of respective liquid filled wells per sub-space.

In another modification an inner surface of at least one of the flexible sheets that forms the space 106 or the sub-space 306 may be coated with one or more reagents to facilitate further multiple reaction conditions. Various surface chemistry techniques can be employed for coating and/or spotting the reagents onto the inner surface of the sheets.

The method further includes a step of determining the results of the said reactions using an optical detection process or a similar process. To optically determine the results at least one of the sheets and one of the clamping plates may be substantially optically transparent. A transparent plate may provide a lensing component of the optical detection system. That system may comprise an optical camera or other light detection unit.

Use of the proposed method and system may provide a digital quantitative result. The result for each of the wells is determined independent of other wells and an overall result obtained by recording, e.g. counting, results across the wells in the space or the sub-spaces. Integration of the entire workflow into one system with a single filling step, or at least only a small number of filling steps, reduces user intervention and increases the time taken to obtain the results. Device cost may also be reduced, particularly where the flexible sheets are provided as part of a disposable cartridge.

One or more modifications of the method described herein may be combined as per the desired reaction conditions.

Without deviating from the present invention the method may be adapted for other biological reactions or chemical reactions. For example, the method may be used for conducting the molecular biology reactions such as nucleic acid amplification reactions. Therefore, one or more reagents coated in the inner surface of flexible sheets may include primer(s) and the liquid contains may contain enzymes such as polymerases, helicases, transcriptase etc. and other reaction machinery. Both isothermal and non-isothermal amplification protocols may be used. The method of the present invention can therefore include, but need not be limited to polymerase chain reaction (PCR), nucleic acid sequence-based amplification (NASBA), loop-mediated isothermal amplification (LAMP), helicase-dependent amplification (HDA), Blocker Displacement Amplification (BDA), rolling circle amplification (RCA), recombinase polymerase amplification (RPA) and similar molecular biology techniques. The result may include digital quantitative and/or qualitative read-outs. Hence, the present invention has an application in nucleic acid amplification tests (NAATs). Also, being rapid, simple and easy to handle the method may be used as a Point of Care (PoC) diagnostic tool.

As an example, the method of present invention may be modified to be used for digital PCR (dPCR). A liquid containing reagents for a dPCR reaction, for example target molecule, is introduced into a space formed in between a pair of flexible sheets. A localised pressure is applied across the sheets to partition the sample liquid into multiplicity of liquid filled wells such that either zero, one or more target molecules are present in each well. An end-point PCR reaction is carried in each well which is then analysed for the presence of a signal for example, a florescence signal of sequence-specific DNA probes or intercalating dyes denoting a positive reaction and absence of signal denoting a negative reaction. Hence, a single positive signal is detected readily over a strong background of negatives. As the PCR reaction is partitioned randomly, it is possible that a positive reaction contains more than one target molecule. To account for micro reactions with more than one template sequence statistical analysis may be applied.

A system capable of carrying out a method of performing parallel reactions as described herein may include a liquid supply mechanism for filling a space between first and second flexible sheets. The flexible sheets may be composed of a biocompatible and inert (bio-inactive) material, optionally polypropylene. The sheets may be pre-treated, i.e., surface passivation to reduce or to negate any hindrance to the reaction. The system further includes a pressure applicator for applying localised pressure across the sheets after filling of the space in order to form a multiplicity of liquid filled wells between the sheets such that neighbouring wells are not in liquid communication with one another. Such wells may be used for carrying out multiple independent reactions in parallel that may be monitored during the course of the reaction. The system may be further equipped with a detector for detecting the results of reactions occurring within respective wells.

FIG. 1 illustrates two flexible sheets 102 and 104 (FIG. 1a) with a space 106 for a liquid 108 (FIG. 1b) and a multiplicity of liquid filled wells 110 formed by the flexible sheets (FIG. 1c).

Depending upon the application, the system may include a heat source to heat-seal the areas of the flexible sheets between the neighbouring wells. The flexible sheets may be composed of thermoplastic material or coated with it such that localised heating creates or enhances a seal by welding together the opposed regions of the flexible sheets.

The heat source may be used for initiating and facilitating the reactions and therefore, for example the heat source may act as a thermal cycler and/or impulse heater.

Figure 3B:
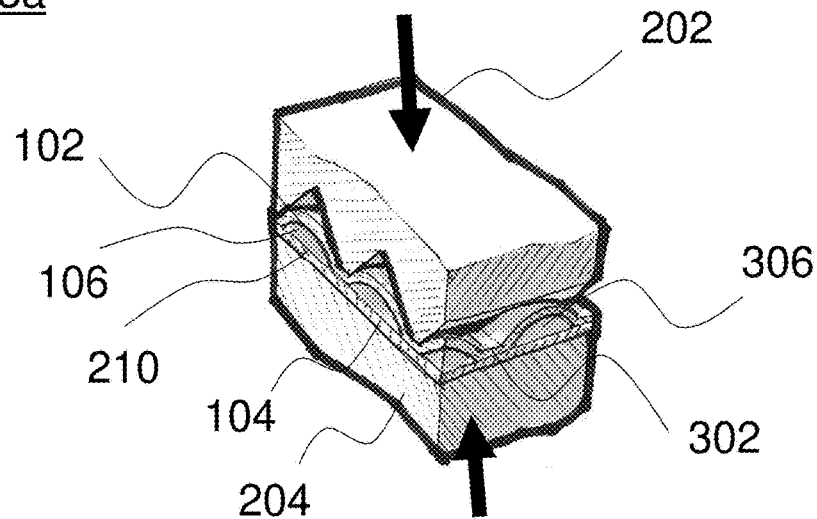

The system may further include a pressure applicator comprising an upper 202 and a lower plate 204, which can be clamped together across the flexible sheets 102/104 to apply localised pressure as illustrated in FIGS. 2 and 3. Either one or both the plates may be associating with the heat source to provide a localised heating corresponding to the regions of localised pressure.

One or both the plates may have a surface profile which defines the regions at which localised pressure and/or heat can be applied across the flexible sheets. Such surface profiles may be uniform thereby defining one or more regular grids. FIG. 2 illustrates cylindrical recesses 208/208' on both upper 202 and lower 204 plate that may be utilized to form a multiplicity of wells 210 in response to the localized pressure applied by the clamping of the plates across the liquid filled flexible sheets. FIG. 3 illustrates a tooth-shaped profile 212 on the upper plate 202 only.

In another modification the flexible sheets may be pre-welded to form compartments/sub-spaces 306 in the space 106 separated by pre-formed joins 302 as exemplified in FIG. 3a. The pre-formed joins ensure that each of the sub-spaces is separated from one another and not in liquid communication with the adjacent sub-space. Each of the sub-spaces 306 may be further associated with one or more inlet/outlet ports to facilitate addition and/or exchange of liquids. Sub-spaces with other shapes may alternatively be provided. For example the space between the sheets may be divided by joins into two halves, four quarters etc.

A system may further include a cartridge comprising an outer housing or frame within which the flexible sheets are located. The cartridge may be a disposable cartridge which is insertable into an analyser unit comprising a liquid supply mechanism, e.g. a micro-fluidic system for injecting a liquid sample or samples into one or more spaces provided between the flexible sheets, a pressure applicator and a detector. Thus, while the cartridge is a disposable unit, analysing unit is reusable.

Figure 4:
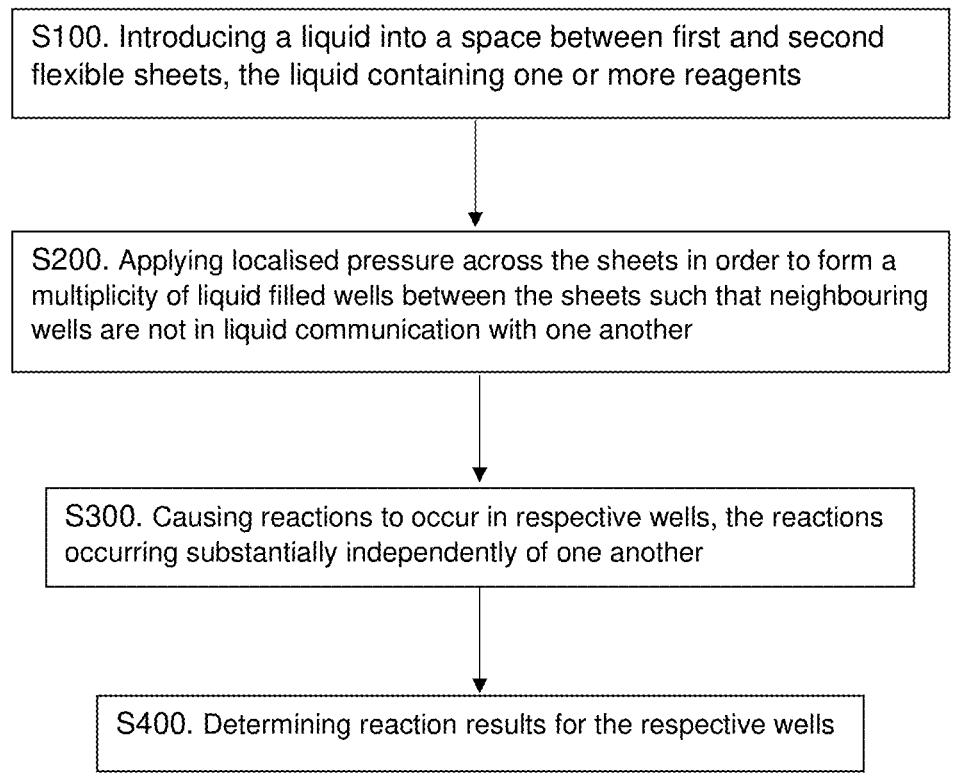
FIG. 4 is a flow diagram illustrating a method according to an embodiment.

FIG. 4 is a flow diagram illustrating a method according to an embodiment and comprising:
  Step 100: Introducing a liquid into a space between first and second flexible sheets, the liquid containing one or more reagents;
  Step 200: Applying localised pressure across the sheets in order to form a multiplicity of liquid filled wells between the sheets such that neighbouring wells are not in liquid communication with one another;
  Step 300: Causing reactions to occur in respective wells, the reactions occurring substantially independently of one another; and
  Step 400: Determining reaction results for the respective wells.

Figure 5:
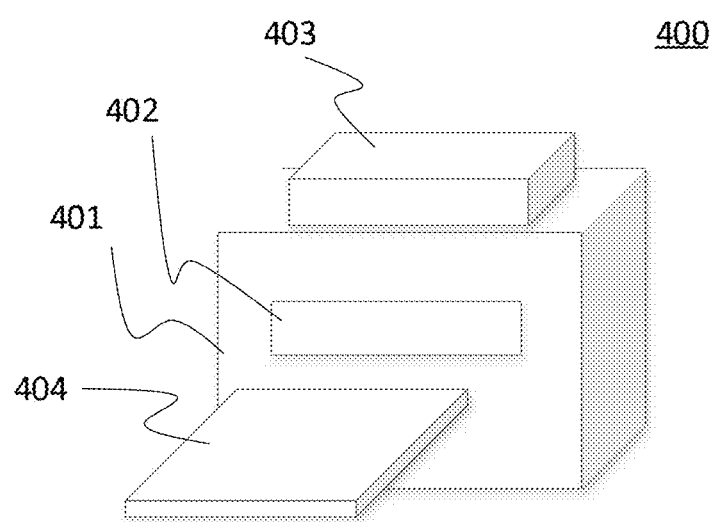
FIG. 5 illustrates a system according to an embodiment.

FIG. 5 illustrates schematically a system 400 according to an embodiment and comprising an analyser unit 401. The unit comprises a main housing containing electronic, electrical and mechanical components, as well as the upper and lower plates described above. The unit also comprises imaging means 403 configured, together with other components of the unit, to capture imaging data. The housing comprises a slot 402 for receiving a cartridge 404, which may be a disposable cartridge. The cartridge 404 may comprise a frame for supporting flexible sheets as described above, as well as defining one or more fluid inlet ports to facilitate injection of a liquid into a space or spaces defined between the flexible sheets.

It will be appreciated by the person of skill in the art that various modifications may be made to the above described method and system without departing from the scope of the present invention.

The invention claimed is:

1. A method of performing multiple parallel reactions, comprising:
   introducing a liquid into a space between flexible sheets, the flexible sheets including a first flexible sheet and a second flexible sheets, the liquid containing one or more reagents;
   applying localised pressure across the flexible sheets in order to form wells that are liquid filled and are between the flexible sheets such that neighbouring wells are not in liquid communication with one another;
   applying heat to the flexible sheets sufficient to heat seal areas of the flexible sheets between neighbouring wells where the localised pressure is applied and to initiate and/or facilitate reactions to occur in respective wells, the reactions occurring substantially independently of one another, a same heat source being used to heat seal areas of the flexible sheets and to initiate and/or facilitate said reactions; and
   determining reaction results for the respective wells.

2. The method of claim 1, wherein the applying applies the heat thermo-cyclically.

3. The method of claim 1, further comprising:
   locating the flexible sheets between upper and lower plates, clamping the upper and lower plates across the flexible sheets in order to apply the localized pressure, and heating at least one of the upper and lower plates in order to heat the flexible sheets.

4. The method of claim 3, wherein at least one of the upper and lower plates has a surface profile which defines regions upon which localised pressure is applied across the flexible sheets.

5. The method of claim 4, wherein the surface profile defines one or more regular grids.

6. The method of claim 3, wherein at least one of the upper and lower plates is transparent.

7. The method of claim 1, wherein the heat seal areas are produced by a welding together of opposed regions of flexible sheets.

8. The method according to of claim 1, wherein the space is one of a plurality of spaces formed between the flexible sheets, the spaces being separated from one another by pre-formed joins between the flexible sheets, and the method being such that a multiplicity of wells are formed within each space.

9. The method of claim 8, wherein the pre-formed joins and defines one or more channels extending between each space and an associated liquid inlet port.

10. The method of claim 1, wherein an inner surface of at least one of the flexible sheets is coated a priori with a reagent or reagents to facilitate said reactions, said inner surface being opposed to an inner surface of the other of the flexible sheets.

11. The method of claim 10, wherein different reagents are coated on the inner surface within respective different spaces to permit different reactions to occur within the wells of different spaces.

12. The method of claim 1, wherein the determining determines the reaction results for the respective wells using an optical detection process, and at least one of the flexible sheets is a substantially optically transparent flexible sheet to permit optical detection across the substantially optically transparent flexible sheet.

13. The method of claim 1, wherein the reactions include nucleic acid amplification, using one of PCR, NASBA, reverse transcription, and LAMP.

14. The method of claim 1, wherein the determining determines a number of wells that have a common reaction result based on the determined reaction results for the respective wells.

* * * * *